United States Patent
Kiani et al.

(10) Patent No.: US 7,274,955 B2
(45) Date of Patent: *Sep. 25, 2007

(54) PARAMETER COMPENSATED PULSE OXIMETER

(75) Inventors: Massl E. Kiani, Laguna Niguel, CA (US); Mohamed Diab, Mission Viejo, CA (US); Ammar Al-Ali, Tustin, CA (US); Walter M. Weber, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 10/671,179

(22) Filed: Sep. 25, 2003

(65) Prior Publication Data

US 2004/0122301 A1    Jun. 24, 2004

Related U.S. Application Data

(60) Provisional application No. 60/413,494, filed on Sep. 25, 2002.

(51) Int. Cl.
*A61B 5/00* (2006.01)
(52) U.S. Cl. .................................... 600/322
(58) Field of Classification Search ............. 600/322, 600/323, 331, 364
See application file for complete search history.

(56) References Cited

U.S. PATENT DOCUMENTS

| | | | |
|---|---|---|---|
| 4,892,101 A | 1/1990 | Cheung et al. | |
| 4,960,128 A | 10/1990 | Gordon et al. | |
| 5,005,576 A | 4/1991 | Gunther | |
| 5,066,859 A | 11/1991 | Karkar et al. | |
| 5,163,438 A | 11/1992 | Gordon et al. | |
| 5,190,039 A * | 3/1993 | Takeuchi et al. | 600/311 |
| 5,337,744 A | 8/1994 | Branigan | |
| 5,372,136 A * | 12/1994 | Steuer et al. | 600/326 |
| 5,431,170 A | 7/1995 | Mathews | |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,725,480 A * | 3/1998 | Oosta et al. | 600/310 |
| D393,830 S | 4/1998 | Tobler et al. | |
| 5,743,262 A | 4/1998 | Lepper, Jr. et al. | |
| 5,758,644 A | 6/1998 | Diab et al. | |

(Continued)

*Primary Examiner*—Eric Winakur
*Assistant Examiner*—Etsub D Berhanu
(74) *Attorney, Agent, or Firm*—Knobbe, Martens, Olson & Bear, LLP

(57) ABSTRACT

A monitor has a primary input responsive to a first property of a tissue site. An uncompensated measurement is determinable from the primary input. A parameter input is responsive to a second property associated with the tissue site, where the first property is dependent upon the second property. The monitor also has a compensation relationship of the primary input, the parameter input and a compensated measurement. A processor is configured to output a compensated measurement from the primary input and the parameter input utilizing the compensation relationship, where the compensated measurement more accurately represents the first property than the uncompensated measurement.

19 Claims, 10 Drawing Sheets

U.S. PATENT DOCUMENTS

| | | |
|---|---|---|
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,842,979 A * | 12/1998 | Jarman ................ 600/322 |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,978,691 A * | 11/1999 | Mills ................... 600/334 |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,104,938 A * | 8/2000 | Huiku et al. ............ 600/322 |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,356,774 B1 | 3/2002 | Bernstein et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,421,549 B1 | 7/2002 | Jacques |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 2002/0133068 A1 * | 9/2002 | Huiku ................ 600/331 |

* cited by examiner

PARAMETER COMPENSATED PULSE OXIMETER

REFERENCE TO RELATED APPLICATIONS

The present application claims priority benefit under 35 U.S.C. §119(e) from U.S. Provisional Application No. 60/413,494, filed Sep. 25, 2002, entitled "Parameter Compensated Pulse Oximeter," which is incorporated herein by reference.

BACKGROUND OF THE INVENTION

Pulse oximetry is a noninvasive, easy to use, inexpensive procedure for measuring the oxygen saturation level of arterial blood. Pulse oximeters perform a spectral analysis of the pulsatile component of arterial blood in order to determine the relative concentration of oxygenated hemoglobin, the major oxygen carrying constituent of blood, and deoxygenated (depleted) hemoglobin. These instruments have gained rapid acceptance in a wide variety of medical applications, including surgical wards, intensive care units, general wards and home care by providing early detection of decreases in the arterial oxygen supply, which reduces the risk of accidental death and injury.

FIG. 1 illustrates a pulse oximetry system 100 having a sensor 110 and a monitor 150. The sensor 110 has emitters 120 and a detector 130. The emitters 120 typically consist of a red LED (light emitting diode) and an infrared LED that project light through blood vessels and capillaries underneath a tissue site, such as a fingernail bed. The detector 130 is typically a photodiode positioned opposite the LEDs so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

Also shown in FIG. 1, the monitor 150 has drivers 152, a sensor front-end 154, a signal processor 155, a display driver 157, a display 158 and a controller 159. The drivers 152 alternately activate the emitters 120 as determined by the controller 159. The front-end 154 conditions and digitizes the resulting current generated by the detector 130, which is proportional to the intensity of the detected light. The signal processor 155 inputs the conditioned detector signal and determines oxygen saturation based upon the differential absorption by arterial blood of the two wavelengths projected by the emitters 120. Specifically, a ratio of detected red and infrared intensities is calculated by the signal processor 155, and an arterial oxygen saturation value is empirically determined based on the ratio obtained, as described with respect to FIGS. 2-3, below. The display driver 157 and associated display 158 indicate a patient's oxygen saturation along with pulse rate.

The Beer-Lambert law provides a simple model that describes a tissue site response to pulse oximetry measurements. The Beer-Lambert law states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \qquad (1)$$

$$\mu_{a,\lambda} = \sum_{i=1}^{n} \epsilon_{i,\lambda} \cdot c_i \qquad (2)$$

where $\mu_{a,\lambda}$ is the bulk absorption coefficient and represents the probability of absorption per unit length. The Beer-Lambert law assumes photon scattering in the solution is negligible. The minimum number of discrete wavelengths that are required to solve EQS. 1-2 are the number of significant absorbers that are present in the solution.

FIG. 2 illustrates top-level computation functions for the signal processor 155 (FIG. 1), described above. For pulse oximetry, it is assumed that wavelengths are chosen such that there are only two significant absorbers, which are oxygenated hemoglobin ($HbO_2$) and deoxygenated hemoglobin (Hb). In particular, pulse oximetry measurements are conventionally made at a red wavelength corresponding to 660 nm and an infrared wavelength corresponding to 940 nm. At these wavelengths, deoxygenated hemoglobin absorbs more red light than oxygenated hemoglobin, and, conversely, oxygenated hemoglobin absorbs more infrared light than deoxygenated hemoglobin.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site also comprises skin, muscle, bone, venous blood, fat, pigment, etc., each of which absorbs light. It is assumed that the background absorption due to these surrounding tissues is invariant and can be ignored. That is, the sensor signal generated by the pulse-added arterial blood is isolated from the signal generated by other layers including tissue, venous blood and baseline arterial blood.

As shown in FIG. 2, to isolate the pulsatile arterial blood, the signal processor 155 (FIG. 1) computes ratios 215, 265 of the AC portions 212, 262 of the detected red (RD) 201 and infrared (IR) 206 signals with respect to the DC portions 214, 264 of the detected signals 201, 206. Computations of these AC/DC ratios 215, 265 provide relative absorption measures that compensate for variations in both incident light intensity and background absorption and, hence, are responsive only to the hemoglobin in the arterial blood. Further, a ratio of the normalized absorption at the red wavelength over the normalized absorption at the infrared wavelength is computed:

$$RD/IR = (Red_{AC}/Red_{DC})/(IR_{AC}/IR_{DC}) \qquad (3)$$

The desired oxygen saturation ($SpO_2$) 282 is then computed empirically from this "red-over-infrared, ratio-of-ratios" (RD/IR) 272. That is, the RD/IR output 272 is input to a look-up table 280 containing empirical data 290 relating RD/IR to $SpO_2$, as described with respect to FIG. 3, below.

FIG. 3 shows a graph 300 depicting the relationship between RD/IR and $SpO_2$. This relationship can be approximated from Beer-Lambert's Law, described above. However, it is most accurately determined by statistical regression of experimental measurements obtained from human volunteers and calibrated measurements of oxygen saturation. The result can be depicted as a curve 310, with measured values of RD/IR shown on a x-axis 302 and corresponding saturation values shown on an y-axis 301. In a pulse oximeter device, this empirical relationship can be stored in a read-only memory (ROM) for use as a look-up table 280 (FIG. 2) so that $SpO_2$ can be directly read-out from an input RD/IR measurement. For example, an RD/IR value of 1.0 corresponding to a point 312 on the calibration curve 310 indicates a resulting $SpO_2$ value of approximately 85%.

SUMMARY OF THE INVENTION

Saturation measurements from a conventional pulse oximeter depend on a predictable, empirical correlation between RD/IR and $SpO_2$. Tissue optical properties, i.e. RD absorbance as compared with IR absorbance, however, vary with other patient dependent parameters such as site temperature, pH and total hematocrit (Hct), to name a few, that are not accounted for in the conventional photon absorbance model. A compensated pulse oximeter advantageously utilizes measurements of one or more parameters that are missing from a conventional pulse oximeter to derive a more accurate $SpO_2$ measurement. Parameter measurements may be derived from multiple parameter sensors, from additional sensors and/or instruments and from manual inputs. A compensated pulse oximeter accounts for these parameters by calibration curve selection, modification or derivation, by measurement output corrections and by dynamic sensor wavelength modification.

DETAILED DESCRIPTION OF THE PREFERRED EMBODIMENT

Overview

Figure 4:
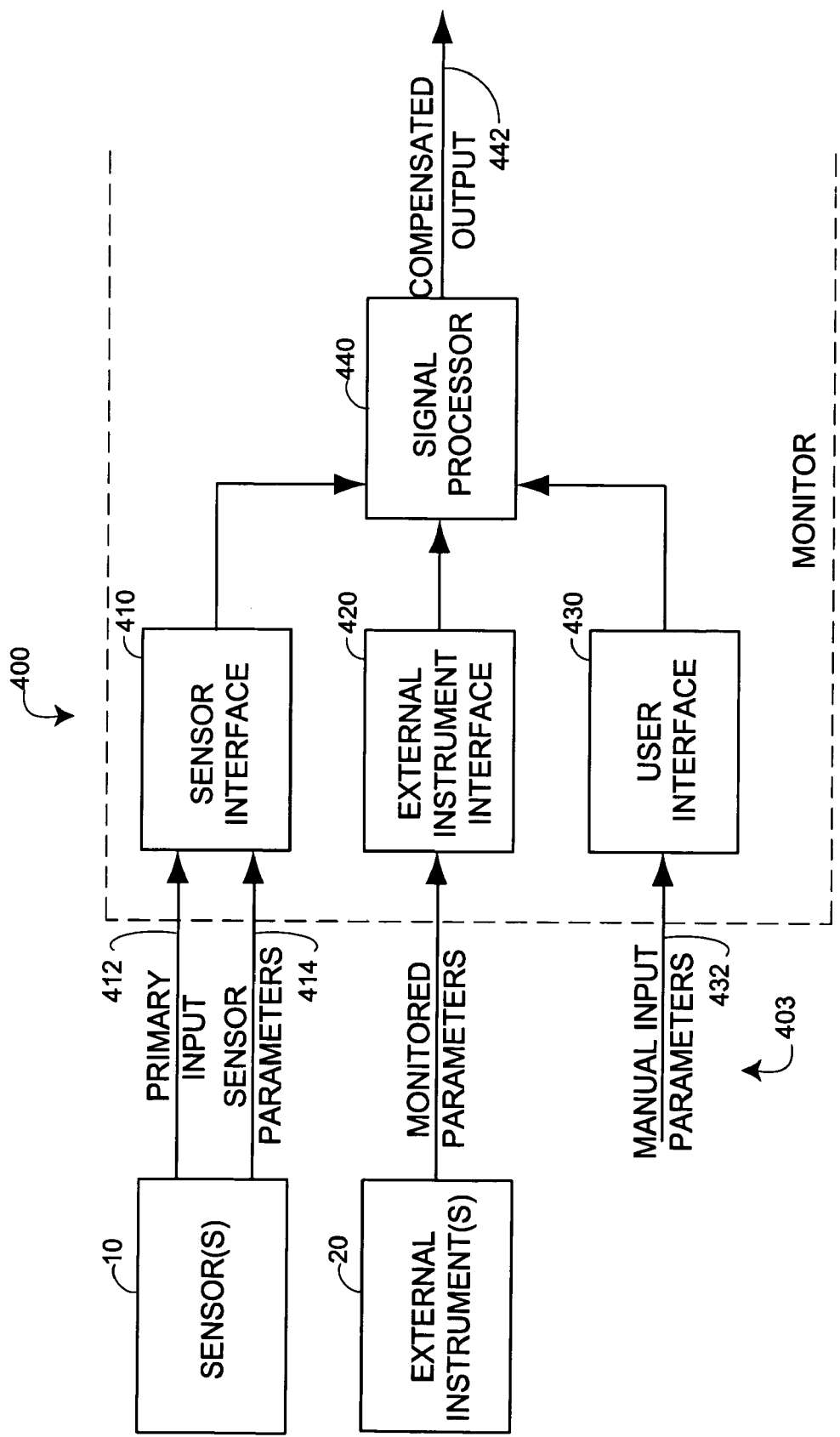
FIG. 4 is a top-level block diagram of a parameter compensated pulse oximeter portion having sensor, external instrument and manual parameter inputs.
Figure 5:
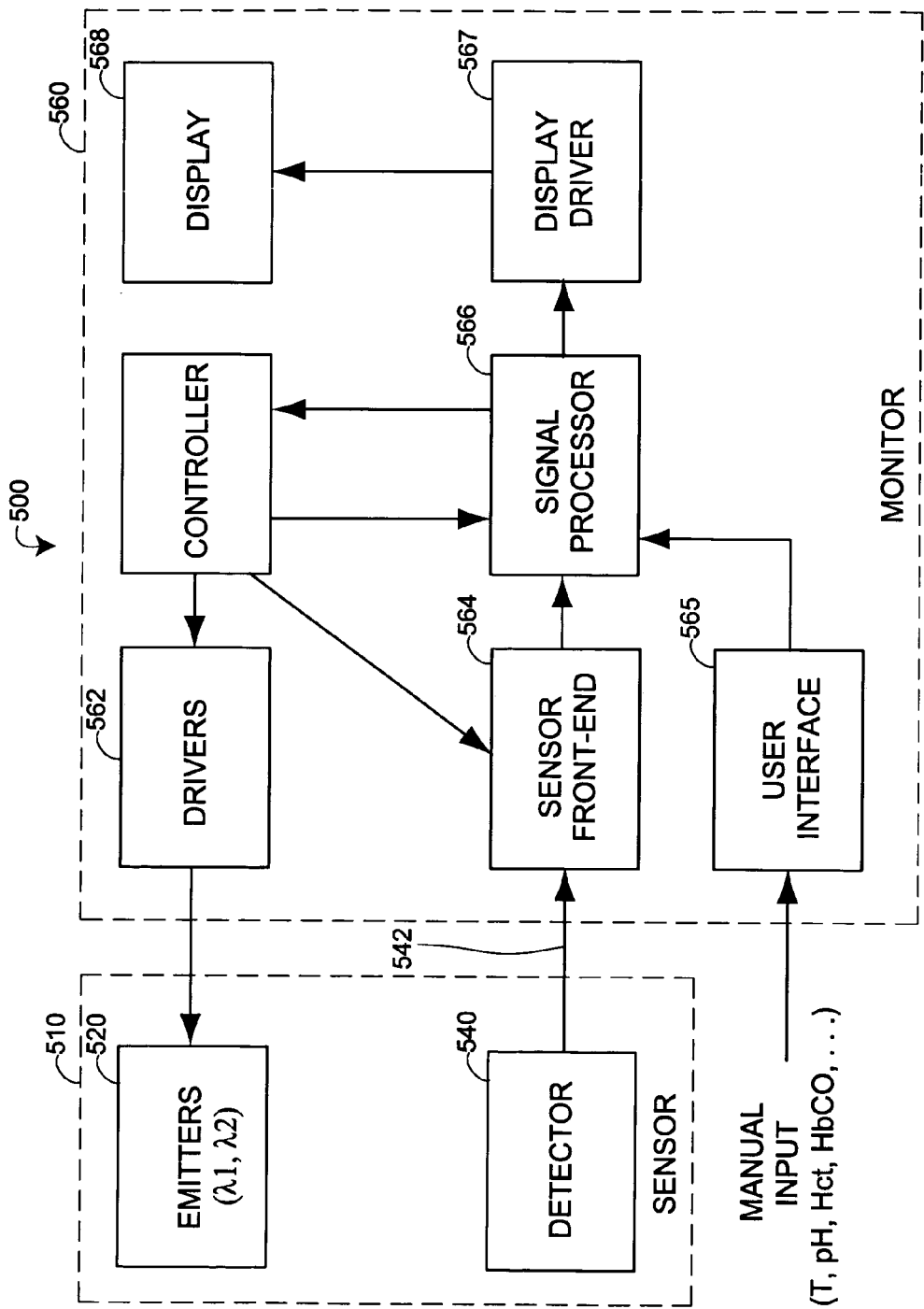
FIG. 5 is a detailed block diagram of a pulse oximeter having manual parameter inputs.
Figure 6:
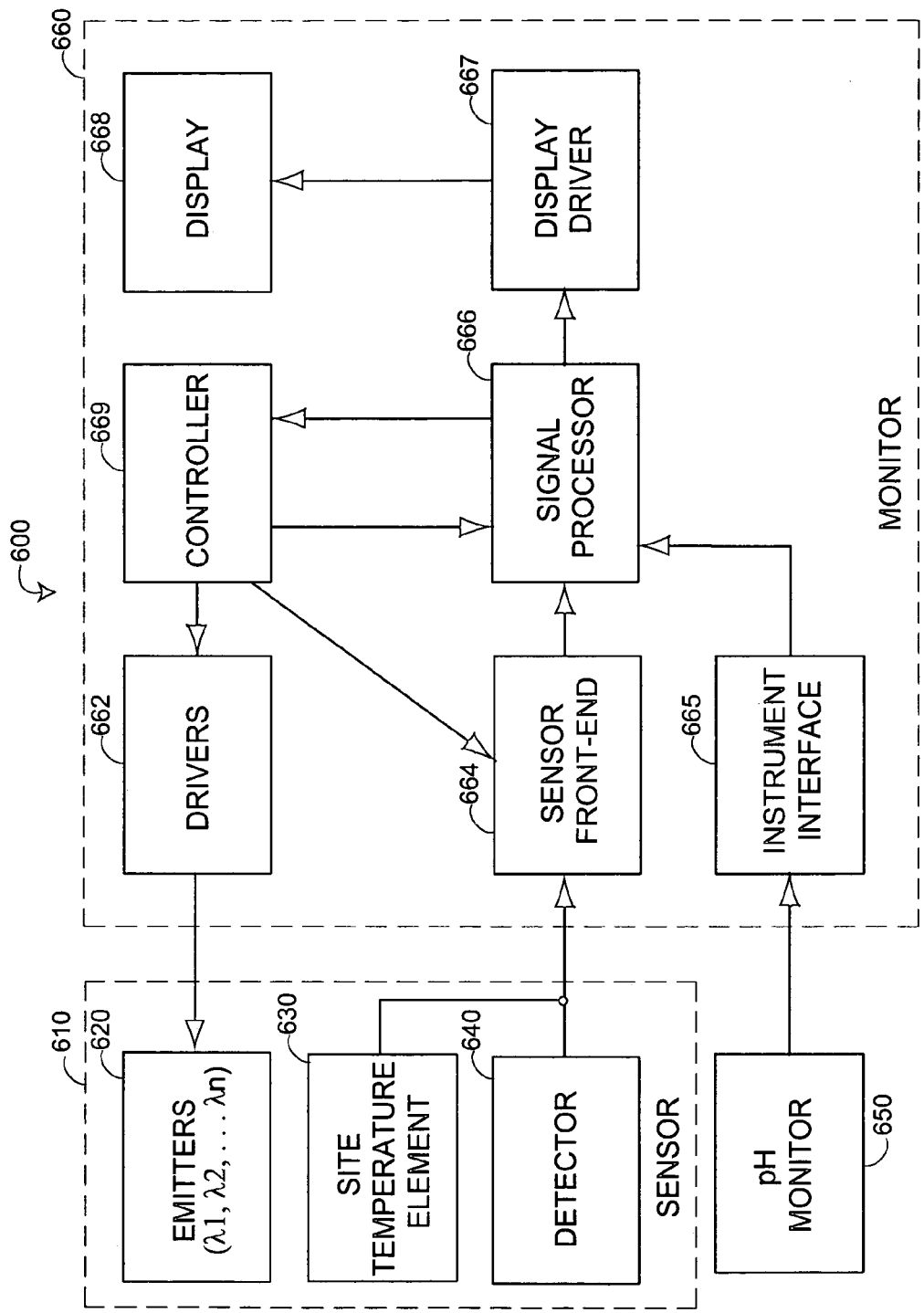
FIG. 6 is a detailed block diagram of a pulse oximeter having a multi-wavelength and site temperature sensor in addition to an external pH monitor input.

Parameter compensated pulse oximetry is described below with respect to monitor interface architectures (FIGS. 4-6) and monitor signal processing functions (FIGS. 7-10). FIG. 4 illustrates a general interface architecture including a primary sensor input for deriving $SpO_2$ and parameter inputs from sensors, external instruments and manual entry for deriving a more accurate $SpO_2$. FIG. 5 illustrates a two-wavelength sensor along with manual parameter inputs. FIG. 6 illustrates a multiple wavelength sensor for a derived parameter input, a sensor temperature element for a site temperature parameter input, and an external instrument parameter input.

Figure 7:
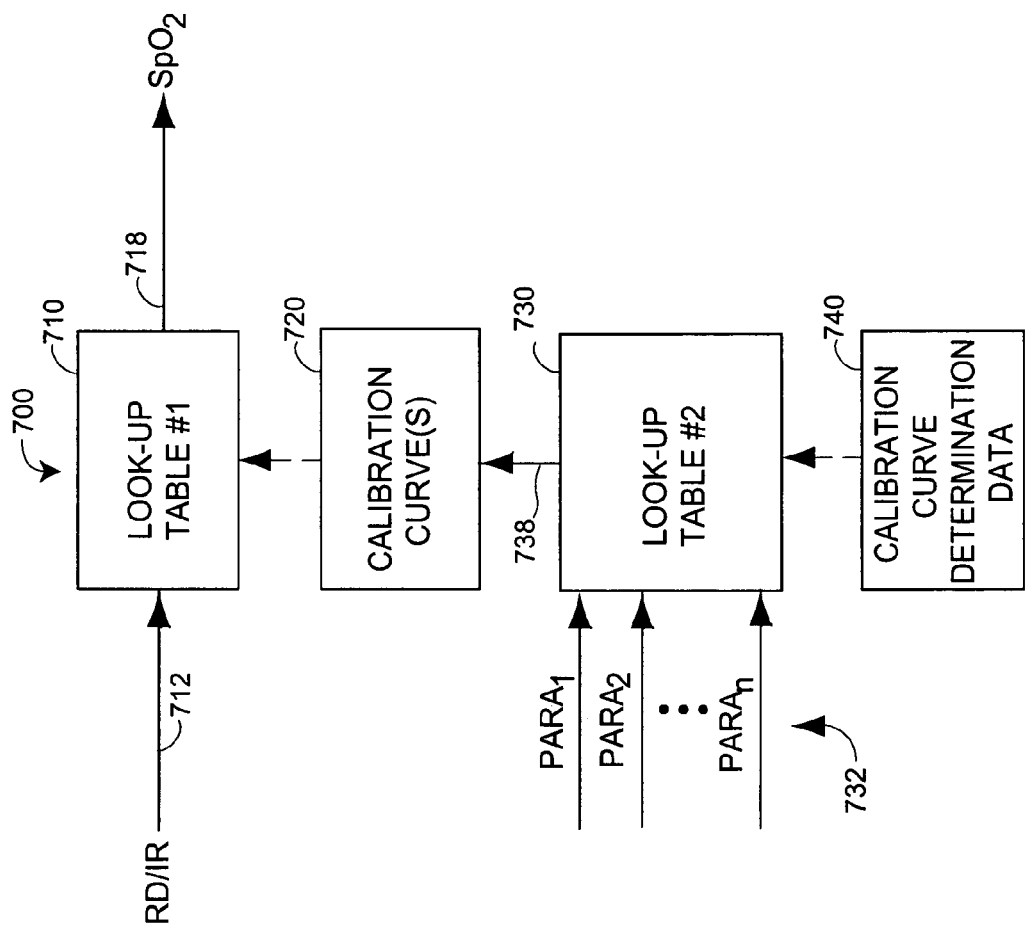
FIG. 7 is a functional block diagram of parameter compensated signal processing incorporating one embodiment of calibration curve determination.
Figure 8:
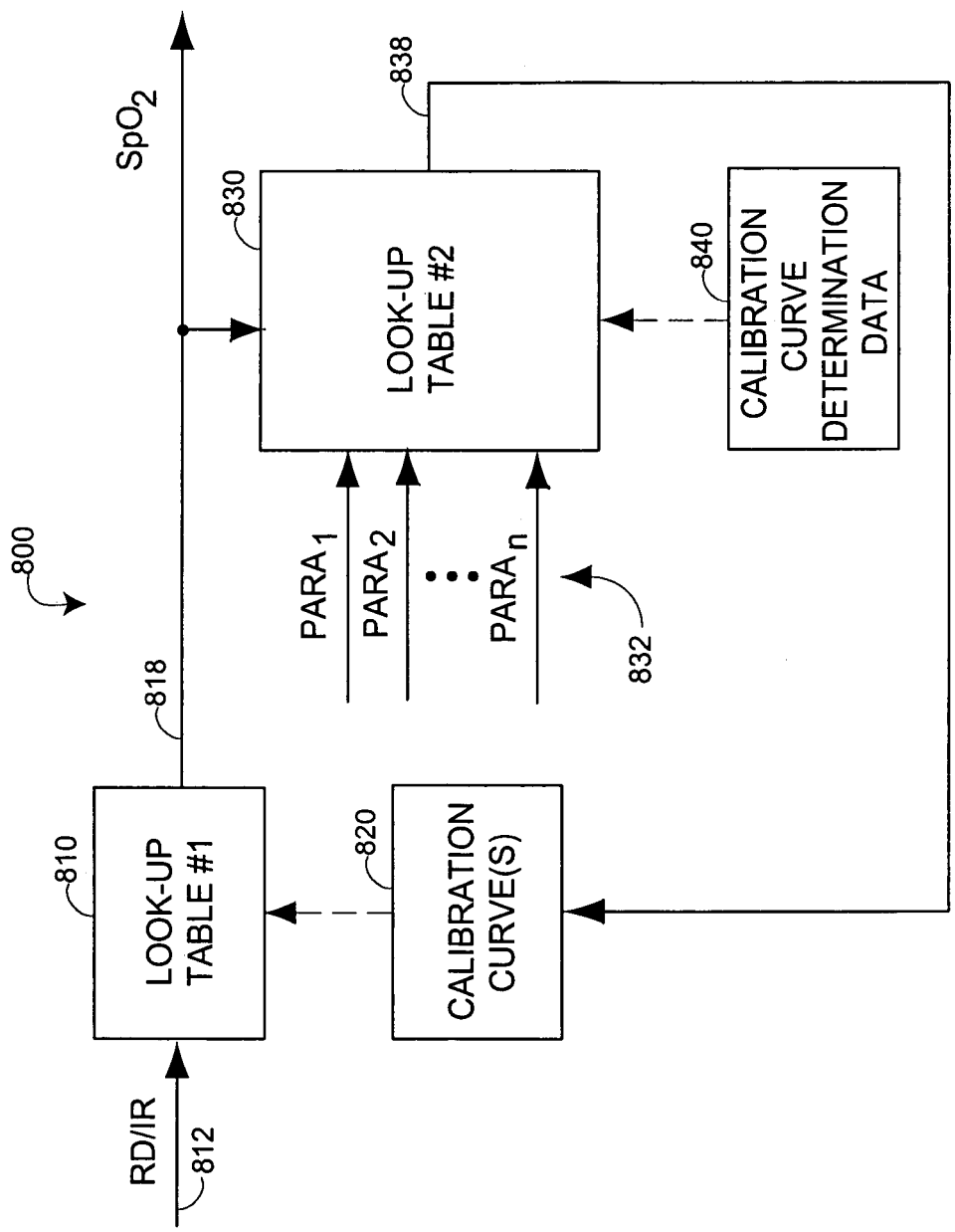
FIG. 8 is a functional block diagram of parameter compensated signal processing incorporating another embodiment of calibration curve determination.
Figure 9:
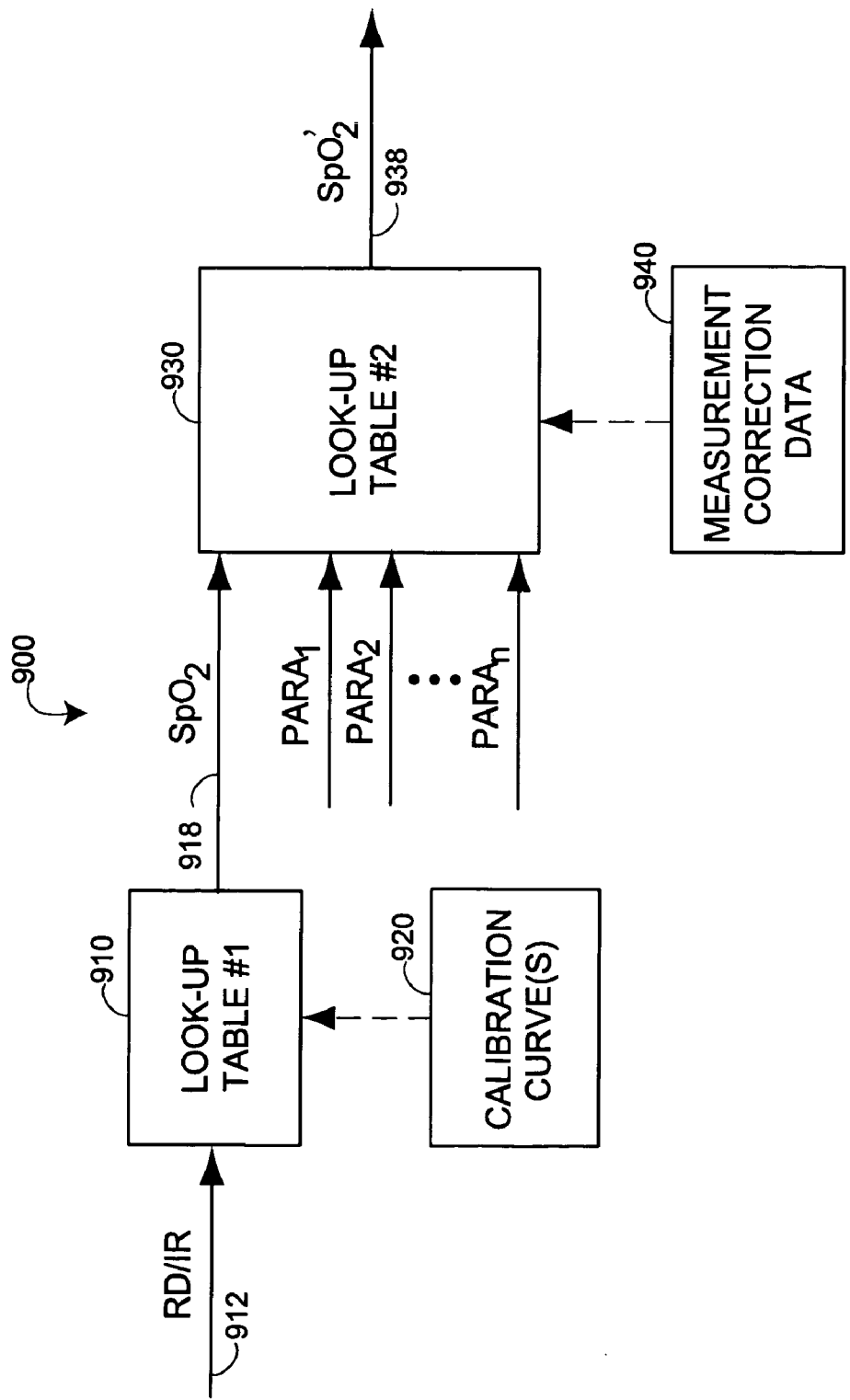
FIG. 9 is a functional block diagram of parameter compensated signal processing incorporating measurement output correction.
Figure 10:
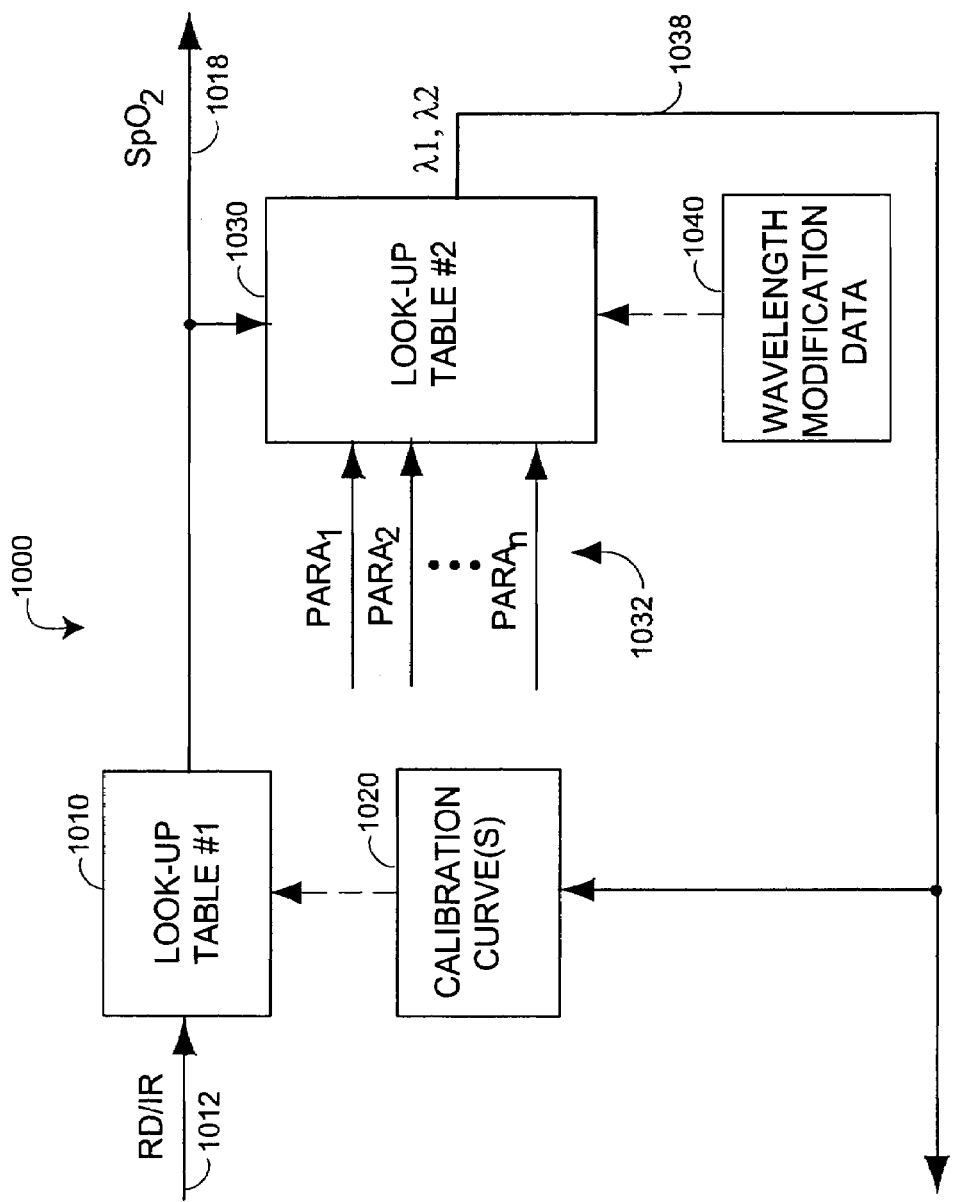
FIG. 10 is functional block diagram of parameter compensated signal processing incorporating sensor wavelength modification.

FIGS. 7-8 illustrate a compensated $SpO_2$ computed from RD/IR utilizing a parameter determined calibration curve. FIG. 9 illustrates a compensated $SpO_2$ computed from parameter dependent correction of an uncompensated $SpO_2$. FIG. 10 illustrates a compensated $SpO_2$ resulting from parameter dependent sensor wavelength modification.

The interface architectures according to FIGS. 4-6 may each support signal processing functions according to FIGS. 7-10. As just one of many examples and embodiments, a pulse oximeter has a manual input compensation parameter, such as described with respect to FIG. 5. The manual input may be, say, a blood gas derived parameter, such as HbCO or MetHb to name just a few. This parameter is utilized to select, modify, derive or otherwise determine a calibration curve so as to compute a more accurate measure of $SpO_2$.

Parameter Compensation Architecture

Figure 1:
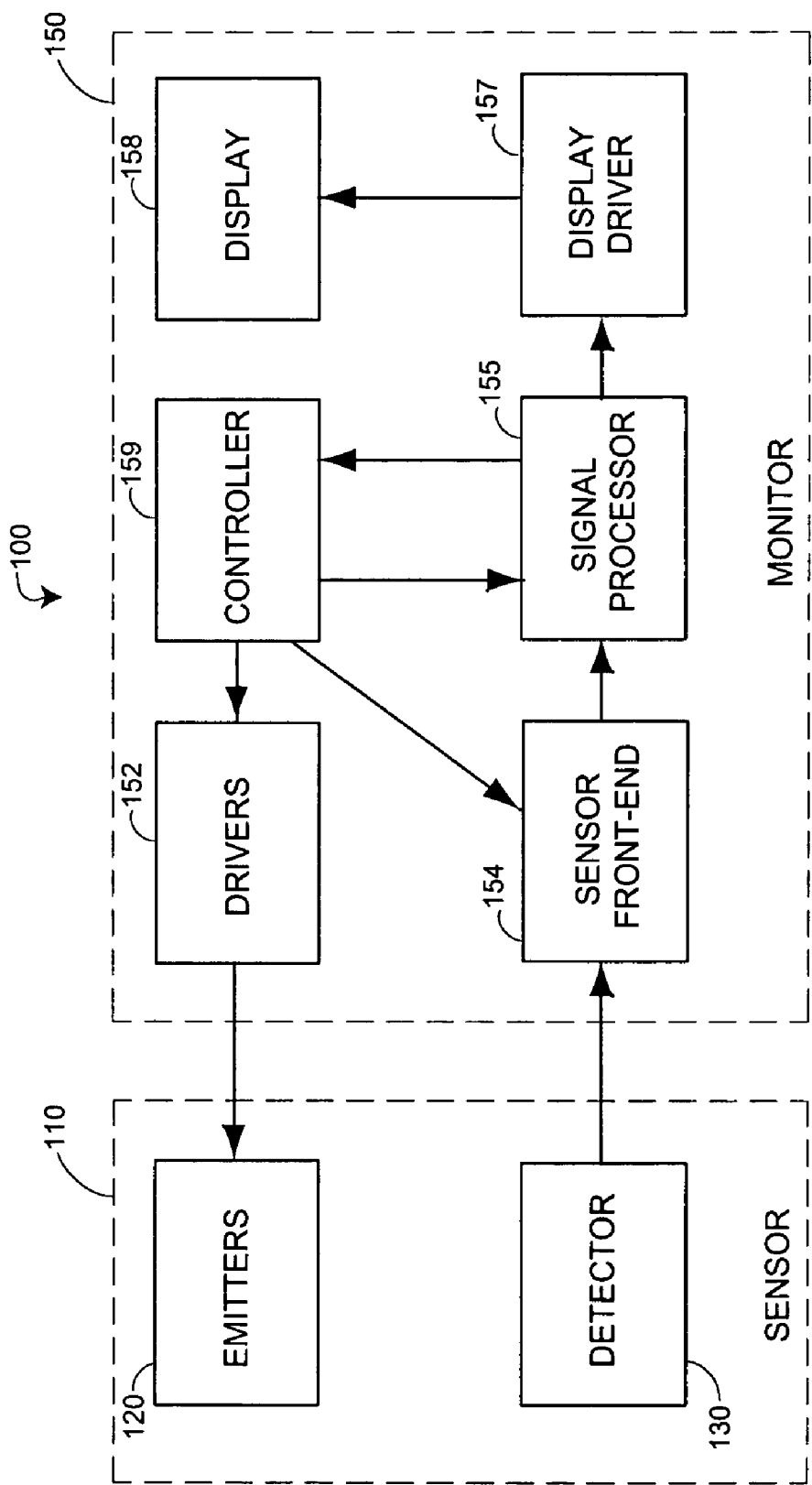
FIG. 1 is a block diagram of a prior art pulse oximeter.
Figure 2:
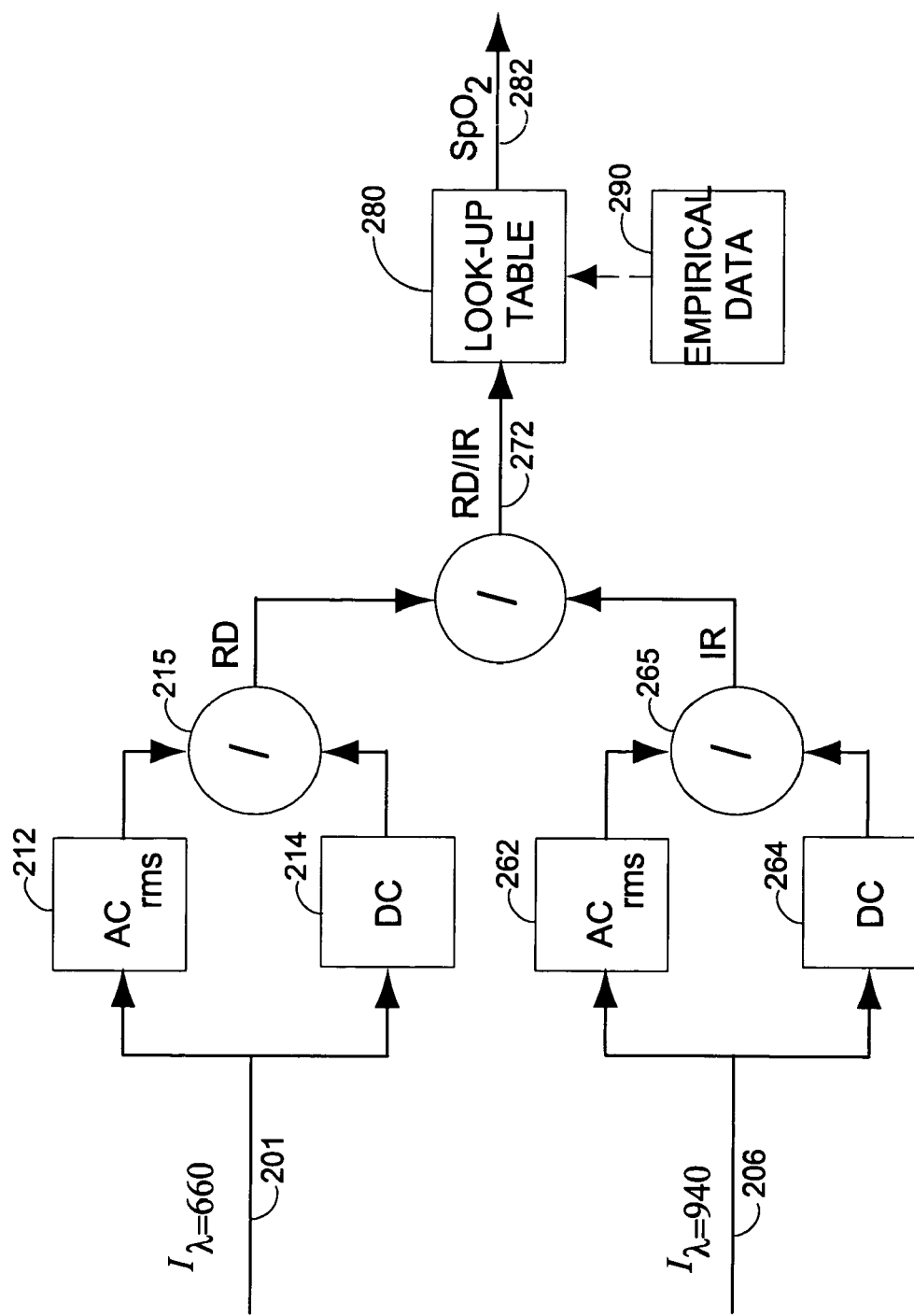
FIG. 2 is a top-level functional diagram of conventional pulse oximetry signal processing.
Figure 3:
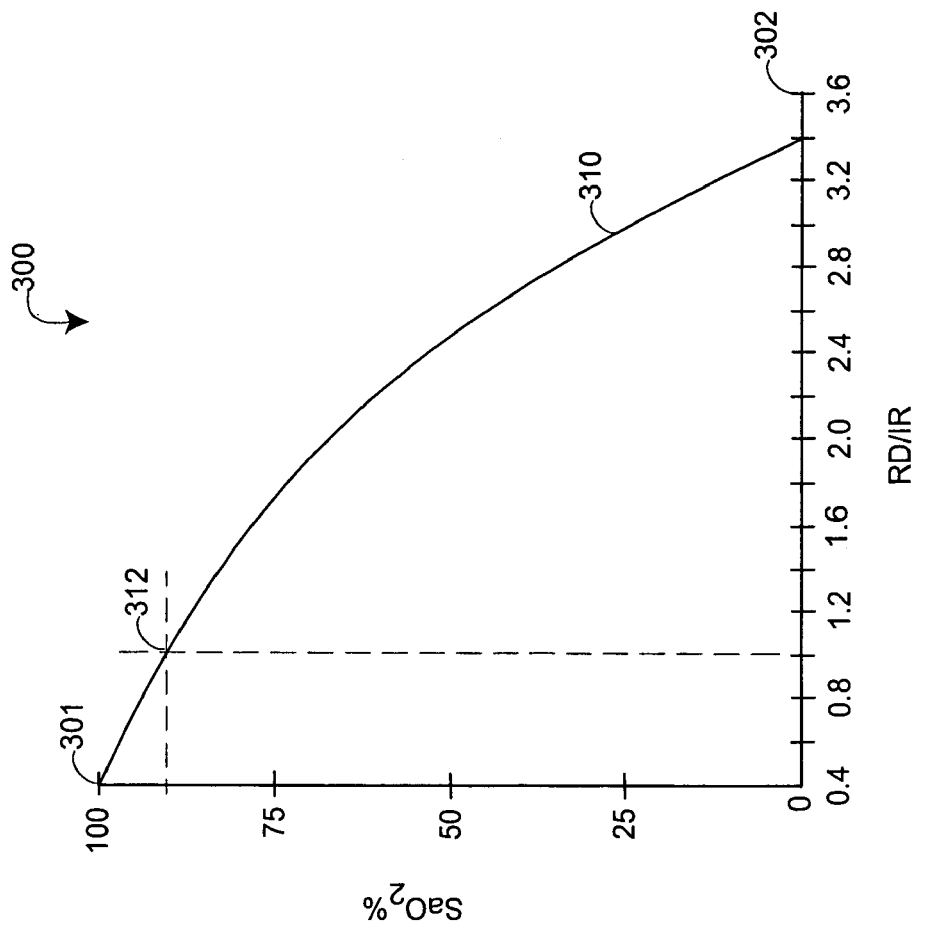
FIG. 3 is an exemplar graph of a conventional calibration curve.

FIG. 4 illustrates a parameter compensated pulse oximeter 400 having a sensor interface 410, an external instrument interface 420 and a user interface 430. The sensor interface 410 connects to one or more tissue site sensors 10, which may be optical or non-optical devices configured to provide invasive or noninvasive measurements of tissue site properties. The sensor interface 410 has a primary input 412 and one or more sensor parameter inputs 414. The primary input 412 is adapted to provide tissue site properties via sensor elements. A sensor parameter input 414 is also adapted to provide tissue site related properties, which include optical or nonoptical properties. In one embodiment, the primary input 412 is a detector response to at least two emitter wavelengths after transmission through or reflection from a tissue site, from which the pulse oximeter may derive at least a conventional measure of oxygen saturation, as described with respect to FIGS. 1-3 above. An example of this embodiment is described with respect to FIG. 5, below. In another embodiment, the sensor 10 utilizes more than two wavelengths so that the pulse oximeter 400 may derive the concentrations of other blood constituents in addition to oxygen saturation, such as total hematocrit (Hct), carboxyhemoglobin (HbCO) and methemoglobin (MetHb), to name a few. An example of this is described with respect to FIG. 6, below. The same sensor or a different sensor provides a measure of tissue site temperature on a sensor parameter input 414, such as described with respect to FIG. 6, below.

Also shown in FIG. 4, an external instrument interface 420 connects to one or more external instruments 20, which may monitor optical or non-optical properties, invasively or noninvasively, from the sensor tissue site or from other portions of a patient or a patient's immediate environment. In one embodiment, the external instrument 20 is a pH monitor, as described with respect to FIG. 6, below.

Further shown in FIG. 4, a user interface 430 accepts one or more manual input parameters 432. As an example, the user interface 430 may be a keyboard input operating in conjunction with a user display, which may range from a small character display to a CRT providing a computer-generated graphical user interface (GUI). The manual inputs may be any information related to a patient or a patient's immediate environment. In one embodiment, a manual input of blood gas measurements, such as are obtainable from a CO-oximeter, is provided. Blood gas measurements may include arterial oxygen saturation ($SaO_2$), Hct, HbCO, MetHb to name a few.

Additionally shown in FIG. 4, the sensor interface 410, external instrument interface 420 and user interface 430 each provide inputs to the signal processor 440. The signal processor utilizes the primary input 412 and one or more parameter inputs 403 to generate a compensated output 442. In one embodiment, the output 442 is an $SpO_2$ measurement that is derived from both the primary input 412 and the parameter inputs 403.

FIG. 5 illustrates one embodiment of a parameter compensated pulse oximeter 500 having a sensor 510 and manual inputs to a monitor 560. In particular, drivers 562 activate emitters 520 that project two wavelengths into a tissue site, and a detector 540 responsive to the emitters 520 provides a primary input 542 to a sensor front-end 564, as described above. A user interface 565 accepts manual inputs such as temperature (T), pH, Hct, HbCO and MetHb to name a few, the values of which a user may obtain from separate instruments. The sensor front-end 564 and user interface 565 output to the signal processor 566 a detector signal along with the manually input parameters. The signal processor 566 computes a compensated $SpO_2$ measurement from the detector signal and these parameters, as described with respect to FIGS. 7-10, below. The compensated $SpO_2$ measurement is then displayed 567, 568 in a manner similar to that described above with respect to FIG. 1.

FIG. 6 illustrates another embodiment of a parameter compensated pulse oximeter 600 having a sensor 610 and an external pH monitor 650 providing inputs to a pulse oximetry monitor 660. The sensor 610 has multiple wavelength emitters 620 and a site temperature element 630. Multiple wavelengths may be achieved, for example, by utilizing multiple LEDs each manufactured for a specific wavelength according to the number of wavelengths desired. Alternatively, one or more LEDs having drive current dependent wavelengths may be utilized, where the drive current is controlled to shift between multiple wavelengths. The site temperature element 630 provides a site temperature parameter input to the sensor front-end 664. In one embodiment, the site temperature element 630 is a thermistor located on the sensor 610 proximate the emitters 620 or proximate the detector 640. The detector 640 provides a multiple wavelength signal output that is combined with a site temperature output to a sensor front-end 664. An instrument interface 665 is adapted to input pH readings from the pH monitor 650. The sensor drivers 662 provide multiplexed activation of the multiple emitters 620 as determined by the controller 669. The signal processor 666 accepts outputs from the sensor front-end 664 and the instrument interface 665. In addition, the signal processor 666 computes an $SpO_2$ measurement from the detector signal along with other blood constituents, utilizing the multiple wavelength signal from the detector 640. Further, the signal processor 666 derives a compensated $SpO_2$ measurement from the input parameters, as described with respect to FIGS. 7-10, below. The compensated $SpO_2$ measurement is then displayed 667, 668 in a manner similar to that described above.

As shown in FIG. 6, a pulse oximetry sensor 610 may be improved for use in conjunction with a parameter compensated pulse oximeter by increasing the number of wavelengths projected by the emitters 620, which allows the resolution of more than two blood constituents, as described above. Further, the sensor 610 may be improved by adding the capability to measure various parameters, such as site temperature. Alternatively, as shown in FIG. 5, pulse oximeter performance can be improved at reduced costs by utilizing simple sensors in conjunction with other instrumentation and/or manual inputs to provide additional input parameters.

The sensor 610 may also have an information element (not shown) that describes information regarding the sensor. In one embodiment, the information element provides the monitor 660 with information regarding available wavelengths for the emitters 620 and/or information regarding the temperature element 630, such as the resistance-temperature characteristics of a thermistor. An information element is described in U.S. Pat. No. 6,011,986 entitled "Manual And Automatic Probe Calibration," assigned to Masimo Corporation, Irvine, Calif. and incorporated by referenced herein.

Parameter Compensation Signal Processing

FIG. 7 illustrates a calibration curve determination function 700 having a first look-up table 710, an associated calibration curve or curves 720, a second look-up table 730 and a calibration curve determination data set 740. The calibration curve determination function 700 advantageously selects, modifies, derives or otherwise determines a calibration curve 720 so as to generate a compensated $SpO_2$ output 718. The first look-up table 710 has an RD/IR input 712 and generates a $SpO_2$ output 718 utilizing a calibration curve 720, such as described with respect to FIGS. 2-3, above. The second look-up table 730 has one or more compensation parameter inputs 732, such as temperature, pH, Hct, HbCO and MetHb to name a few, and provides a calibration curve control output 738 according to calibration curve determination data 740. The control output 738 determines the calibration curve 720 utilized by the first look-up table 710, according to the compensation parameters 732. In one embodiment, the control output 738 selects one of a family of calibration curves 720. In another embodiment, the control output 738 determines the direction and amount of shift in a calibration curve 720 or a selected one of a family of calibration curves 720. In yet another embodiment, the control output 738 modifies a calibration curve or a selected one of a family of calibration curves 720, such as by rotating a calibration curve around a selected point on the curve. In an additional embodiment, the control output 738 specifies one or more points from which a calibration curve 720 is derived. The calibration curves 720 and calibration curve determination data 740 define a relationship between the primary input 712, the parameter inputs 732 and the compensated output 718. The calibration curve or curves 720 and associated curve determination data 740 may be determined by statistical regression of experimental measurements obtained from human volunteers and calibrated measurements of oxygen saturation and associated parameters. All or part of the first look-up table 710, calibration curves 720, second look-up table 730 and calibration curve determination data set 740 may be replaced by or combined with a mathematical formula or algorithm, theoretically or experimentally derived, that derives a calibration curve or curves or directly computes an $SpO_2$ output from RD/IR and parameter inputs.

FIG. 8 illustrates a calibration curve determination function 800 having a first look-up table 810, a calibration curve or curves 820, a second look-up table 830 and associated calibration curve modification data 840. The calibration curve determination function 800 functions as described with respect to FIG. 7, but has, as input to the second look-up table 830, the compensated $SpO_2$ output 818. In particular, the first look-up table 810 has an RD/IR input 812 and generates a $SpO_2$ output 818 utilizing a calibration curve 820. The second look-up table 830 has one or more compensation parameter inputs 832 and has, as an input, the $SpO_2$ output 818. The second look-up table 830 provides a calibration curve control output 838 according to calibration curve determination data 840. The control output 838 determines the calibration curve 820 utilized by the first look-up table 810, according to the compensation parameters 832 and the $SpO_2$ output 818. As described above with respect to FIG. 7, the control output 838 may select one of a family of calibration curves 820, may determine the direction and amount of shift in a calibration curve 820 or a selected one of a family of calibration curves 820, may modify a calibration curve or a selected one of a family of calibration curves 820, such as by rotating a calibration curve around a selected point on the curve, or may specify one or more points from which a calibration curve 820 is derived or may cause a combination of these actions. The calibration curve or curves 820 and associated curve determination data 840 may be determined by statistical regression of experimental measurements obtained from human volunteers and calibrated measurements of oxygen saturation and associated parameters.

In one advantageous embodiment, there is a single parameter input 832 comprising one or more blood gas measurements of $SaO_2$. According to these $SaO_2$ measurements, a calibration curve 820 is selected, modified, such as by shifting or rotating a calibration curve, or otherwise derived so that subsequently derived $SpO_2$ measurements are consistent with blood gas measurements. In a particular embodiment, so as to reduce sensitivity, multiple blood gas input values are taken over a range of saturation values and are evaluated for consistency within a tolerance range before the current calibration curve is replaced or modified.

FIG. 9 illustrates a parameter compensation function 900 for an uncompensated $SpO_2$ measurement having a first look-up table 910, a calibration curve or curves 920, a second look-up table 930 and associated correction data 940. The parameter compensation function 900 differs from the calibration determination function 700 (FIG. 7) described above in that, as shown in FIG. 9, an uncompensated $SpO_2$ value 918 is calculated and corrected to yield a compensated $SpO_2'$ value 938. This contrasts with a compensated $SpO_2$ value being directly derived from RD/IR, as described with respect to FIG. 7, above. In one embodiment, the parameter compensation function 900 advantageously upgrades the results of a conventional pulse oximeter. The first look-up table 910 and calibration curve 920 may be as described with respect to FIGS. 2-3, above. The second look-up table 930 and associated correction data 940 may be as described with respect to FIG. 7, above, except that an uncompensated value of $SpO_2$ 918 is an input to the look-up table 930 rather than RD/IR 912. As above, the correction data set 940 may be determined by statistical regression of experimental measurements obtained from human volunteers and calibrated measurements of oxygen saturation and associated parameters or may be replaced by or combined with a mathematical formula or algorithm that directly computes a compensated $SpO_2$ output from uncompensated $SpO_2$ and parameter inputs.

In one advantageous embodiment, a blood gas measurement of HbCO and/or MetHb is manually entered into a pulse oximeter and utilized to generate a compensated value of $SpO_2$. As described above, conventional pulse oximetry utilizes two wavelengths, assuming that Hb and $HbO_2$ are the only significant absorbers. However, carboxyhemoglobin (HbCO) and methemoglobin (MetHb) may also be significant absorbers at RD and IR wavelengths. The presence of significant concentrations of HbCO and MetHb have different effects on a conventional pulse oximeter estimate of oxygen saturation. $HbO_2$ and HbCO have similar extinctions at the RD wavelength, as do MetHb and Hb. At the IR wavelength, HbCO is relatively transparent whereas MetHb has greater extinction than the other hemoglobins. The two wavelength assumption has the effect of lumping $HbO_2$ and HbCO together, i.e. HbCO is counted as an oxygen carrying form of hemoglobin, causing a conventional pulse oximeter to overestimate oxygen saturation. As MetHb increases, RD/IR tends to unity and $SpO_2$ to a constant (e.g. 85%) regardless of oxygen saturation. A manually entered value of HbCO and or MetHb is used as a parameter in conjunction with the functions described above with respect to any of FIGS. 7-9, so as to distinguish these hemoglobin species from $HbO_2$ and Hb, providing a more accurate, HbCO and/or MetHb compensated, value of $SpO_2$.

FIG. 10 illustrates a wavelength modification function 1000 having a first look-up table 1010, a calibration curve or curves 1020, a second look-up table 1030 and associated wavelength modification data 1040. The wavelength modification function 1000 advantageously changes sensor wavelength to generate a compensated $SpO_2$ output 1018. The first look-up table 1010 has an RD/IR input 1012 and generates an $SpO_2$ output 1018 utilizing conventional calibration curves 1020. The wavelength control output 1038 provides a calibration curve input for selecting a wavelength dependent calibration curve 1020. The second look-up table 1030 has $SpO_2$ 1018 and parameter 1032 inputs and provides a sensor wavelength control output 1038 according to associated wavelength modification data 1040. As above, the look-up tables may be replaced by or combined with mathematical formulas or algorithms. The wavelength control output 1038 is a feedback path to a controller 669 (FIG. 6) and/or drivers 662 (FIG. 6). In one advantageous embodiment, there are no parameter inputs 1032, and the wavelength control output 1038 is dependent on $SpO_2$. In this manner, sensor wavelength can be dynamically adjusted based upon saturation levels, e.g. a first red and/or IR wavelength may be used in low saturation conditions and a second red and/or IR wavelength may be used in normal saturation conditions.

A parameter compensated pulse oximeter has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of monitoring a blood constituent value comprising the steps of:
   determining a relationship between a blood constituent value, a biological property and a compensated measurement of said blood constituent value;
   reading a primary input in communication with a first device responsive to said blood constituent value;
   reading a parameter input in communication with a second device responsive to said biological property;
   wherein said first device comprises an optical device and said second device comprises a non-optical device;
   processing said primary input and said parameter input according to said relationship to as to determine said compensated measurement of said blood constituent value; and
   causing an output indicative of said compensated measurement of said blood constituent value to be displayed.

2. The monitoring method of claim 1, wherein the step of determining a relationship further comprises determining a calibration curve based on the biological property and wherein processing said primary input and said parameter input according to said relationship so as to output said compensated measurement further comprises using said calibration curve.

3. The monitoring method of claim 2, wherein the step of determining a relationship further comprises determining a relationship between the blood constituent value, the biological property, the compensated measurement and a previously obtained compensated measurement and wherein processing said primary input and said parameter input according to said relationship so as to output said compensated measurement further comprises processing said previously obtained compensated measurement.

4. The monitoring method of claim 1, wherein the step of determining a relationship further comprises altering a calibration curve based on the biological property and wherein processing said primary input and said parameter input according to said relationship so as to output said compensated measurement further comprises using said calibration curve.

5. The monitoring method of claim 4, wherein altering comprises one or more of shifting, rotating, and modifying said calibration curve.

6. The monitoring method of claim 1, wherein said second biological property comprises pH.

7. A monitor comprising:
a first input means in communication with a first device for determining blood constituent values;
a second input means in communication with a second device for determining biological property values;
wherein said first device comprises an optical device and said second device comprises a non-optical device;
a compensation means for determining a relationship between compensated measurement values of said blood constituent, said blood constituent values and said biological property values; and
a processor means for deriving a compensated measurement of said blood constituent values from said first input means, said second input means and said compensation means.

8. The monitor of claim 7, wherein said second biological property comprises pH.

9. A monitor for compensating a first physiological property using a second physiological property, the monitor comprising:
a primary input in communication with a first device configured to measure a first physiological property;
a parameter input in communication with a second device and configured to measure a second physiological property; and
a processor configured to determine a compensated measurement of said first physiological property from said primary input and said parameter input utilizing a compensation relationship between said primary input and said parameter input;
wherein said first device comprises an optical device and said second device comprises a non-optical device.

10. The monitor of claim 9, wherein said first property is dependent upon said second property.

11. The monitor of claim 9, wherein said first physiological property comprises blood oxygen levels.

12. The monitor of claim 9, wherein said second physiological property comprises pH.

13. The monitor of claim 9, wherein said second physiological property comprises Hct.

14. The monitor of claim 9, wherein said second physiological property comprises HbCO.

15. The monitor of claim 9, wherein said second physiological property comprises MetHb.

16. The monitor of claim 9, wherein said compensation relationship comprises a calibration curve.

17. The monitor of claim 9, wherein the first device comprises an information element.

18. A monitor for compensating a first physiological property using a second physiological property, the monitor comprising:
a primary input in communication with a first device configured to measure a first physiological property;
a parameter input in communication with a second device and configured to measure a second physiological property; and
a processor configured to determine a compensated measurement of said first physiological property from said primary input and said parameter input utilizing a compensation relationship between said primary input and said parameter input;
wherein said second physiological property comprises pH.

19. A monitor for compensating a first physiological property using a second physiological property, the monitor comprising:
a primary input in communication with a first device and responsive to a first physiological property;
a parameter input in communication with a second device and responsive to a second physiological property; and
a processor configured to output a compensated measurement of the first physiological property from said primary input and said parameter input utilizing a compensation relationship between said primary input and said parameter input;
wherein said second physiological property comprises Hct.

* * * * *